United States Patent
Klausner et al.

(10) Patent No.: US 10,239,035 B2
(45) Date of Patent: Mar. 26, 2019

(54) SOLAR THERMOCHEMICAL REACTOR, METHODS OF MANUFACTURE AND USE THEREOF AND THERMOGRAVIMETER

(71) Applicant: UNIVERSITY OF FLORIDA RESEARCH FOUNDATION, INC., Gainesville, FL (US)

(72) Inventors: James F. Klausner, Gainesville, FL (US); Joerg Petrasch, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 189 days.

(21) Appl. No.: 15/384,837

(22) Filed: Dec. 20, 2016

(65) Prior Publication Data
US 2017/0217771 A1     Aug. 3, 2017

Related U.S. Application Data

(62) Division of application No. 14/367,495, filed as application No. PCT/US2012/071332 on Dec. 21, 2012, now Pat. No. 9,669,379.

(Continued)

(51) Int. Cl.
*C01B 3/10* (2006.01)
*B01J 19/08* (2006.01)
(Continued)

(52) U.S. Cl.
CPC ............. *B01J 19/087* (2013.01); *B01J 8/42* (2013.01); *B01J 19/02* (2013.01); *B01J 19/127* (2013.01);
(Continued)

(58) Field of Classification Search
None
See application file for complete search history.

(56) References Cited

U.S. PATENT DOCUMENTS

| 4,030,890 A | 6/1977 | Diggs |
| 4,115,927 A | 9/1978 | Rosensweig |

(Continued)

FOREIGN PATENT DOCUMENTS

| DE | 2735767 A1 | 3/1979 |
| JP | H10279955 A | 10/1998 |

(Continued)

OTHER PUBLICATIONS

Abanades, Stéphane et al., "CO2 splitting by thermo-chemical looping based on ZrxCe1-xO2 oxygen carriers for synthetic fuel generation" Fuel, vol. 102, Dec. 2012, pp. 180-186, Special Section: ACS Clean Coal.

(Continued)

*Primary Examiner* — Kishor Mayekar
(74) *Attorney, Agent, or Firm* — Thomas | Horstemeyer, LLP

(57) ABSTRACT

A solar thermochemical reactor includes an outer member, an inner member disposed within an outer member, wherein the outer member surrounds the inner member and wherein the outer member has an aperture for receiving solar radiation and wherein an inner cavity and an outer cavity are formed by the inner member and outer member and a reactive material capable of being magnetically stabilized wherein the reactive material is disposed in the outer cavity between the inner member and the outer member.

5 Claims, 7 Drawing Sheets

Related U.S. Application Data

(60) Provisional application No. 61/579,449, filed on Dec. 22, 2011.

(51) Int. Cl.
  *B01J 8/42*  (2006.01)
  *B01J 19/12*  (2006.01)
  *F24S 20/20*  (2018.01)
  *B01J 19/02*  (2006.01)
  *C01B 3/04*  (2006.01)
  *G01N 25/02*  (2006.01)

(52) U.S. Cl.
  CPC ............ *C01B 3/042* (2013.01); *C01B 3/105* (2013.01); *F24S 20/20* (2018.05); *G01N 25/02* (2013.01); *B01J 2208/00451* (2013.01); *B01J 2219/0263* (2013.01); *B01J 2219/085* (2013.01); *B01J 2219/1203* (2013.01); *Y02E 10/41* (2013.01); *Y02E 60/364* (2013.01)

(56) References Cited

U.S. PATENT DOCUMENTS

| | | | |
|---|---|---|---|
| 4,292,171 A | 9/1981 | Mayer et al. | |
| 4,319,893 A | 3/1982 | Hatch et al. | |
| 4,430,254 A | 2/1984 | Passariello | |
| 5,143,668 A | 9/1992 | Hida | |
| 5,863,850 A | 1/1999 | Nawa | |
| 6,633,042 B1 | 10/2003 | Funken et al. | |
| 6,780,457 B2 | 8/2004 | Baumann et al. | |
| 7,033,570 B2 | 4/2006 | Weimer et al. | |
| 7,140,181 B1 | 11/2006 | Jensen et al. | |
| 8,110,174 B2 | 2/2012 | Kodama | |
| 8,187,731 B2 | 5/2012 | Weimer | |
| 8,388,706 B2 | 3/2013 | Ugolin | |
| 2003/0208959 A1 | 11/2003 | Weimer et al. | |
| 2005/0175533 A1 | 8/2005 | Thomas et al. | |
| 2006/0229476 A1 | 10/2006 | Mitchell et al. | |
| 2008/0089834 A1 | 4/2008 | Kodama | |
| 2008/0236389 A1 | 10/2008 | Leedy et al. | |
| 2009/0142578 A1 | 6/2009 | Riman et al. | |
| 2009/0232725 A1 | 9/2009 | Aaron | |
| 2010/0140154 A1 | 6/2010 | Colon et al. | |
| 2010/0303692 A1 | 12/2010 | Perkins et al. | |
| 2011/0048690 A1 | 3/2011 | Reppel et al. | |
| 2011/0136027 A1 | 6/2011 | Chen et al. | |
| 2012/0295113 A1 | 11/2012 | Kurizoe | |
| 2012/0302436 A1 | 11/2012 | Vormberg | |
| 2013/0266502 A1 | 10/2013 | Lichty et al. | |
| 2014/0291570 A1 | 10/2014 | Klausner | |
| 2015/0321158 A1 | 11/2015 | Klausner | |

FOREIGN PATENT DOCUMENTS

| | | |
|---|---|---|
| KR | 20110037329 A | 4/2011 |
| KR | 20110077154 A | 7/2011 |
| WO | WO9600125 A1 | 1/1996 |
| WO | WO03004942 A1 | 1/2003 |
| WO | WO03076334 A1 | 9/2003 |
| WO | 2010041014 A1 | 4/2010 |

OTHER PUBLICATIONS

Coker et al.; "Ferrite-YSZ composites for solar thermochemical production of synthetic fuels: in operando characterization of CO2 reduction"; J.Mater.Chem; 21; 2011, 10767-10776.

DE2735767 Published Mar. 1, 1979; Machine Translation; 19 Pages.

Diver et al.; "Testing of a CR5 Solar Thermochemical Heat Engine Prototype", Proceedings of the ASME 2010 4th International Conference on Energy Sustainability, May 2010, pp. 1-8.

Diver, Richard B. et al., "Solar Thermochemical Water-Splitting Ferrite-Cycle Heat Engines", J. Sol. Energy Eng., Nov. 2008, vol. 130, Issue 4, 041001 (8 pages).

European Extended Search Report for EP Application No. 12859196. 3; dated Dec. 1, 2015 (6 pages).

European Extended Search Report for EP Application No. 13865853. 9; dated Aug. 19, 2016 (5 pages).

Evans, Lindsey R. et al., "Materials Development for the CR5 Solar Thermochemical Heat Engine", ASME 2006 International Solar Energy Conference (ISEC2006), Jul. 8-13, 2006 , Denver, Colorado, USA Sponsor: Solar Energy Division, Solar Energy, Paper No. IS.

Extended European Search Report for EP Application No. 12811990. 6; dated Feb. 2, 2015 (6 pages).

Gokon et al., "Monoclinic zirconia-supported Fe3O4 for the two-step water-splitting thermochemical cycle at high thermal reduction temperatures of 1400-1600° C.", International Journal of Hydrogen Energy, vol. 34, Issue 3, Feb. 2009,pp. 1208-1217.

Gokon, Nobuyuki et al., "Ferrite/zirconia-coated foam device prepared by spin coating for solar demonstration of thermochemical water-splitting", International Journal of Hydrogen Energy, vol. 36, Issue 3, Feb. 2011, pp. 2014-2028.

Gokon, Nobuyuki et al., "Thermochemical two-step water-splitting for hydrogen production using Fe-YSZ particles and a ceramic foam device", Energy, vol. 33, Issue 9, Sep. 2008, pp. 1407-1416.

Guillot, Stéphanie, et al. "Corrosion effects between molten salts and thermal storage material for concentrated solar power plants", Applied Energy, vol. 94, Jun. 2012, pp. 174-181.

Herrmann, Ulf, et al. "Two-tank molten salt storage for parabolic trough solar power plants", Energy, vol. 29, Issues 5-6, Apr.-May 2004, pp. 883-893.

International Preliminary Report on Patentability for Application No. PCT/US2012/045698 filed Jul. 6, 2012; dated Jan. 23, 2014; 5 pages.

International Preliminary Report on Patentability for Application No. PCT/US2012/071332 filed Dec. 21, 2012; dated Jun. 24, 2014; 7 pages.

International Preliminary Report on Patentability for International Application No. PCT/US2013/076037 International Filing date Dec. 18, 2013; Report dated Jun. 23, 2015; 6 pages.

International Search Report for Application No. PCT/US2012/ 045698 filed Jul. 6, 2012; dated Jan. 21, 2013; 5 pages.

International Search Report for Application No. PCT/US2012/ 071332 filed Dec. 21, 2012; dated Apr. 29, 2013; 5 pages.

International Search Report for International Application No. PCT/ US2013/076037 International Filing date Dec. 18, 2013; Report dated Apr. 4, 2014; 5 pages.

Kodama et al.; "A Two-Step Thermochemical Water Splitting by Iron-Oxide on Stabilized Zirconia", Journal of Solar Energy Engineering, vol. 128, No. 1, Jan. 2006, 5 pages.

Kodama, T. et al. "Thermochemical hydrogen production by a redox system of ZrO2-supported Co(II)-ferrite", Solar Energy, vol. 78, Issue 5, May 2005, Solar Hydrogen pp. 623-631.

Lichty , Paul et al., "Atomic layer deposited thin film metal oxides for fuel production in a solar cavity reactor", International Journal of Hydrogen Energy, vol. 37, Issue 22, Nov. 2012, pp. 16888-16894.

Mehdizadeh, Ayyoub M., "Enhancement of thermochemical hydrogen production using an iron-silica magnetically stabilized porous structure", International Journal of Hydrogen Energy, vol. 37, Issue 11, Jun. 2012, pp. 8954-8963.

Meier, Anton et al., "Solar chemical reactor technology for industrial production of lime" Solar Energy 80 (2006) 1355-1362.

Roeb, Martin, et al. "Materials-Related Aspects of Thermochemical Water and Carbon Dioxide Splitting: A Review" Materials 2012, 5(11), 2015-2054; Published: Oct. 24, 2012.

Wieckert, C. "Design Studies for a Solar Reactor Based on a Simple Radiative Heat Exchange Model" Journal of Solar Energy Engineering, Aug. 2005, vol. 127; pp. 425-429.

Written Opinion for Application No. PCT/US2012/045698 filed Jul. 6, 2012; dated Jan. 21, 2013; 5 pages.

Written Opinion for Application No. PCT/US2012/071332 filed Dec. 21, 2012; dated Apr. 29, 2013; 6 pages.

(56) References Cited

OTHER PUBLICATIONS

Written Opinion for International Application No. PCT/US2013/076037 International Filing date Dec. 18, 2013; Report dated Apr. 4, 2014; 5 pages.

Yang, Zhen, et al. "Thermal analysis of solar thermal energy storage in a molten-salt thermocline", Solar Energy, vol. 84, Issue 6, Jun. 2010, pp. 974-985.

Zhu, Xing, et al. "Hydrogen and syngas production from two-step steam reforming of methane over $CeO_2$—$Fe_2O_3$ oxygen carrier", Journal of Rare Earths, vol. 28, Issue 6, Dec. 2010, pp. 907-913.

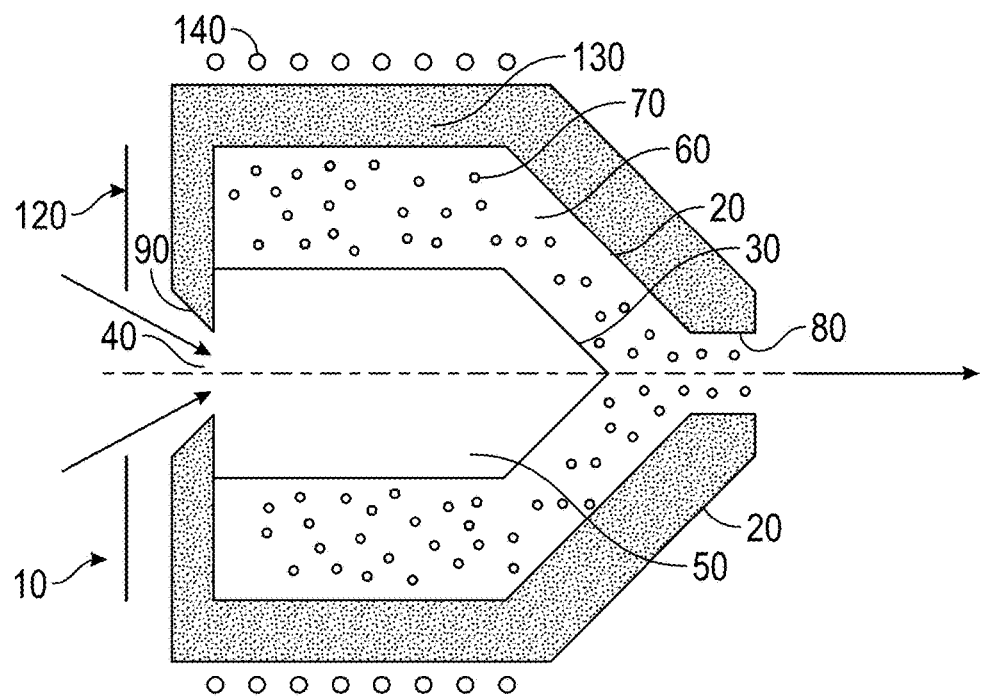
FIG. 2A
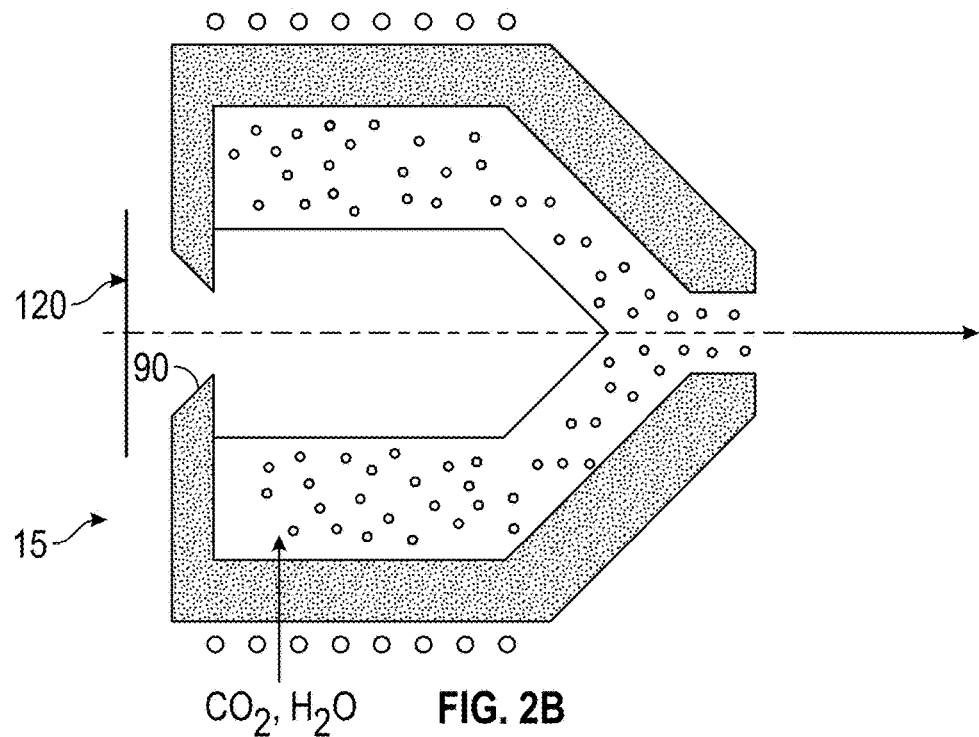
CO₂, H₂O  FIG. 2B

SOLAR THERMOCHEMICAL REACTOR, METHODS OF MANUFACTURE AND USE THEREOF AND THERMOGRAVIMETER

CROSS REFERENCE TO RELATED APPLICATIONS

This application claims the benefit of US National Stage application Ser. No. 14/367,495, filed Jun. 20, 2014, which claims the benefit of International Application No. PCT/US2012/071332, filed on Dec. 21, 2012, which claims the benefit of U.S. Application No. 61/579,449, filed on Dec. 22, 2011, which is incorporated herein by reference in their entirety.

STATEMENT REGARDING FEDERALLY SPONSORED RESEARCH OR SUPPORT

This invention was made with Government support under DE-AR0000184 awarded by the U.S. Department of Energy. The Government has certain rights in this invention.

BACKGROUND

This disclosure relates to a solar thermochemical reactor, methods of manufacture, and uses thereof and a thermogravimeter.

Solar thermochemistry is a newly emerging technology for the production of fuels using highly concentrated solar radiation. Solar power is used to facilitate thermochemical reactions. Solar thermochemical reactors are in the early stages of development. Significant challenges are posed by the use of solar energy as a renewable energy source, which makes it difficult to deploy on a large scale. Solar energy is, by its nature, transient as it is dependent upon exposure to the sun. Solar thermochemical reactions can proceed at very high temperatures. Solar chemical reactors can also employ a window manufactured from an optically transparent material (e.g., glass, plastic, or combinations thereof) to admit highly concentrated radiation to the reaction site. The optically transparent material can be structurally weak and extremely susceptible to staining and subsequent damage due to thermal stresses. In addition, thermochemical reactions can result in sintering of the reactant materials that reduces their internal surface area and adversely affects the chemical kinetics of the reaction.

It is therefore desirable to develop solar thermochemical reactors which operate under lower temperature conditions, do not use a window that is manufactured from an optically transparent material and facilitate control of the chemical kinetics of the thermochemical reaction. It is also desirable to develop a method of using solar thermochemical reactors in a manner which maximizes the availability of solar energy during non-transient periods.

SUMMARY

Disclosed herein is a solar thermochemical reactor comprising an outer member, an inner member disposed within and surrounded by the outer member, wherein the outer member has an aperture for receiving solar radiation, an inner cavity and an outer cavity formed by the inner and outer members, respectively, and a reactive material capable of being magnetically stabilized wherein the reactive material is disposed in the outer cavity between the inner member and the outer member.

Disclosed herein too is a method of making a solar thermochemical reactor comprising disposing an inner member within an outer member that surrounds the inner member wherein the outer member has an aperture for receiving solar radiation and disposing a reactive material capable of being magnetically stabilized between the inner member and the outer member.

Disclosed herein too is a method of using a solar thermochemical reactor comprising disposing an inner member within an outer member, wherein the outer member surrounds the inner member, disposing a reactive material capable of being magnetically stabilized in between the outer member and the inner member, applying a vacuum to the outer member, fluidizing the reactive material, applying a magnetic field at least partially around the outer member; disposing solar radiation onto the outer member, carrying out a reduction reaction in the reactor, extracting oxygen from the outer member; disposing carbon dioxide and water onto the reactor material, carrying out an oxidation reaction in the reactor and extracting carbon monoxide gas and hydrogen gas from the outer member.

Disclosed herein too is a cycling loop process for producing synthetic gas comprising disposing a first solar thermochemical reactor in close proximity to a second solar thermochemical reactor, focusing solar radiation from a concentrated source onto the first solar thermochemical reactor, carrying out a reduction reaction in the first solar thermochemical reactor, focusing solar radiation from the concentrated source onto a second solar thermochemical reactor, and carrying out a reduction reaction in the second solar thermochemical reactor wherein the first reactor and second reactor each comprise an outer member having an aperture for receiving solar radiation, wherein said outer member completely surrounds an inner member, wherein the outer member and inner member form an inner cavity and outer cavity and further wherein a reactor material capable of becoming magnetically stabilized is disposed in the outer cavity.

Disclosed herein too is a solar thermogravimeter for modeling the kinetics of thermochemical reactions in a solar thermochemical reactor comprising a metal pressure vessel, a tubular or dome shaped quartz vessel for optical access, a low vibration vacuum pump, an analytical balance disposed within the low pressure vessel, a temperature sensor, a thermocouple, a flow meter and a gas phase chromatograph or mass spectrometer.

BRIEF DESCRIPTION OF THE FIGURES

FIG. 2A is a depiction of a cross section of an exemplary solar thermochemical reactor in which a reduction reaction occurs;

FIG. 2B is a depiction of a cross section of an exemplary solar thermochemical reactor in which an oxidation reaction occurs;

DETAILED DESCRIPTION

Figure 1A:
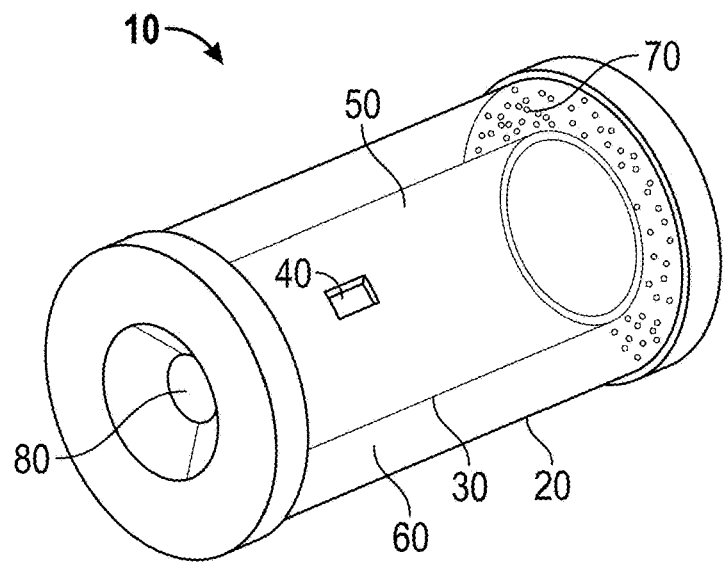
FIG. 1A is a depiction of an exemplary solar thermochemical reactor.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," "upper" or "top," and "inner" or "outer" may be used herein to describe one element's relationship to another element as illustrated in the Figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower," can therefore, encompass both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The transition term "comprising" encompasses the transition terms "consisting of" and "consisting essentially of."

Various numerical ranges are disclosed herein. These ranges are inclusive of the endpoints as well as numerical values between these endpoints. The numbers in these ranges and those on the endpoints are interchangeable.

Solar energy is the most abundant source of renewable energy. Because solar energy is an intermittent power source, storage of this energy is desirable for large-scale deployment and production of fuels. Solar thermochemistry can be used to produce synthetic gas ("syngas"), a precursor used for the production of clean and carbon neutral synthetic hydrocarbon fuels such as methanol, methane or synthetic petroleum. Solar thermochemistry can also be used to store concentrated solar energy in chemical energy carriers until production of syngas or fuel is desired. Thermochemical storage of concentrated solar energy is desirable because chemical energy carriers have a high energy density, are stable, can be stored indefinitely; and a complete infrastructure for their transport and storage already exists, i.e., the existing infrastructure for hydrocarbon fuel transport and storage.

Solar thermochemical reactors can have windowed in which the window is manufactured from an optically transparent material. Such windowed designs present reliability issues due to weakness in mechanical structure and staining and limit the size of reactors, making it difficult to scale up solar reactor technology to an industrial level. In addition, metal reactor materials used in solar thermochemical reactors can be subject to undesirable sintering, which reduces the surface area of the metal reactor materials and causes the period during which the metal reactor materials are used for repeated reactor reaction cycles to become significantly reduced. The thermochemical reactions which are carried out in solar reactors also involve significant periods of time. For example, a single cycle to produce syngas using reduction and oxidation can take up to five hours.

Two-step metal oxide looping processes involve a reduction reaction and an oxidation reaction to complete one "redox" cycle. The direct thermolysis of water can involve temperatures in excess of 2500° C. Two-step metal oxide looping processes can be advantageous because they avoid these extreme temperatures. Two-step metal oxide looping processes using volatile metal oxides such as zinc oxide can have disadvantages associated with avoiding recombination of the highly reactive gaseous metal-oxygen mixture produced. Such processes can also involve high temperatures to carry out the solar reduction/metal disassociation step.

Disclosed herein are reactors, methods of manufacture and use thereof and thermogravimeters which address one or more of the above-described challenges. Disclosed herein is a solar thermochemical reactor comprising an outer member, an inner member disposed within and surrounded by the outer member, wherein the outer member has an aperture for receiving solar radiation, an inner cavity and an outer cavity formed by the inner and outer members, respectively and a reactive material capable of being magnetically stabilized wherein the reactive material is disposed in the outer cavity between the inner member and the outer member.

Disclosed herein too is a method of making a solar thermochemical reactor comprising disposing an inner member disposed within an outer member that surrounds the inner member wherein the outer member has an aperture for receiving solar radiation and disposing a reactive material capable of being magnetically stabilized between the inner member and the outer member.

In an exemplary embodiment, as depicted in FIG. 1A, the solar thermochemical reactor 10 comprises an outer member 20, an inner member 30 disposed within the outer member 20 wherein the outer member 20 completely surrounds the sides, top and bottom of the inner member 30, and further wherein the outer member 20 has an aperture 40 for receiving solar radiation. An inner cavity 50 is formed inside the inner member 30 and an outer cavity 60 is formed in between the inner member 30 and the outer member 20. The inner cavity 20 allows solar radiation in, and the radiation is trapped within the cavity and eventually absorbed by the cavity walls. A reactive material 70 capable of being magnetically stabilized is disposed in the outer cavity 60. The outer member 20 further comprises a material port 80 from which reaction products are extracted and reactant materials may be introduced. The inner and outer members 20, 30 of the reactor are of any shape known to those of skill in the art, specifically a cylindrical shape. In an exemplary embodiment, the reactor 10 comprises a single inner member 30, a single outer member 20, a single inner cavity 50 and a single outer cavity 60.

The use of an aperture 40 with the dual cavity design overcomes the structural weakness and efficiency problems associated with the use of optically transparent materials (e.g., glass, plastic, or combinations thereof) in windows in reactor systems. Accordingly, the reactor 10 has an aperture 40 which is devoid of an optically transparent material. In an embodiment, the aperture 40 comprises a media that has a refractive index of about 1.0 to about 1.05. In another embodiment, the aperture 40 comprises a media that has a density of about 0.90 to about 1.50 kg/m$^3$. In yet another embodiment, the aperture 40 comprises a fluid. In an exemplary embodiment, the aperture 40 comprises a fluid wherein the fluid is air.

Figure 1B:
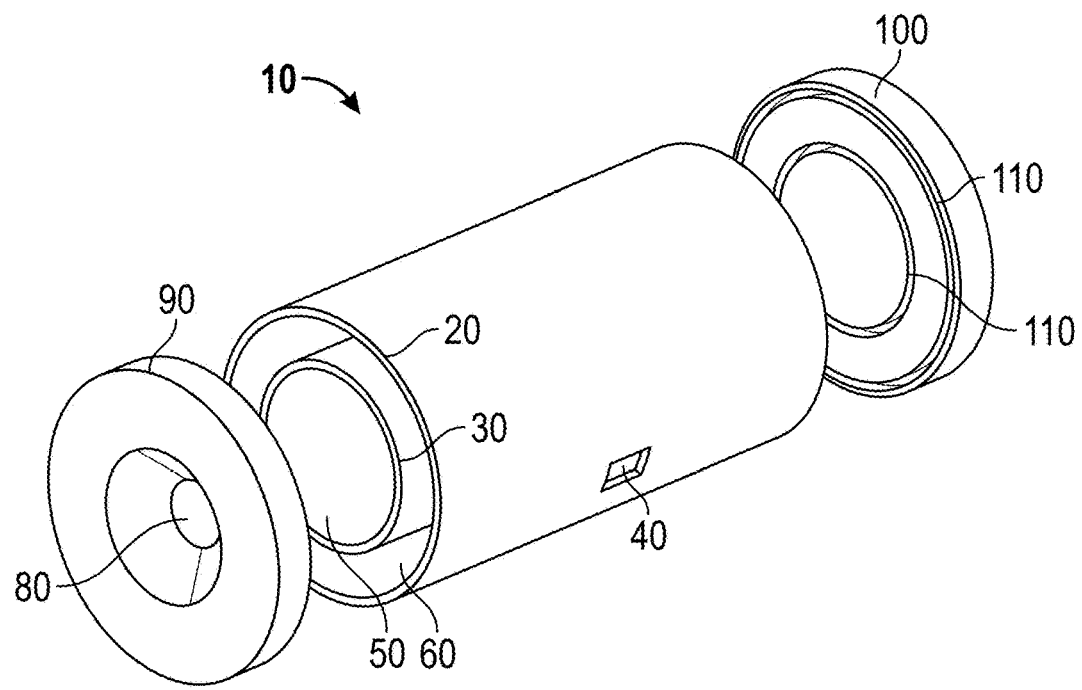
FIG. 1B is a depiction of another exemplary solar thermochemical reactor.

In another exemplary embodiment, as depicted in FIG. 1B, the outer member 20 of the reactor assembly 10 further comprises a front plate 90 which is detachable from a first end of the outer member 20 which surrounds the inner member 30. The outer member 20 also further comprises a rear plate 100 is detachable from a second end of the outer member 20. The second end is opposed to the first end. The front plate 90 and/or rear plate 100 are used to facilitate the loading of reactive materials (capable of becoming magnetically stabilized) into the outer cavity 60 and unloading of spent reactive materials from the outer cavity 60. The front plate 90 and/or rear plate 100 are formed to fit over the inner member 30 and outer member 20, thereby also covering the inner cavity 50 and the outer cavity 60. The front plate 90 and rear plate 100 comprise grooved seals 110 that form a self-aiding fit over the ends of the inner member 30 and outer member 20. In an embodiment, the outer member 20 is used in conjunction with a vacuum pump to tightly seal the assembled parts of the reactor. The reactor 10 has a vacuum line running from the outer member 20 of the reactor to a vacuum pump (not shown). The vacuum pump is in fluid communication with the reactor 10. Alternatively, in another embodiment, the outer member 20 is formed such that it completely surrounds the inner member 30 without having a front plate 90 and/or rear plate 100. In other words, the outer member 20 and the inner member 30 are formed in a single piece with ports to introduce and remove materials from them.

In an embodiment, the outer member 20 further comprises a shutter which exposes or covers the aperture 40 in the outer member 20 for receiving solar radiation as desired. The shutter 120 can be seen in the FIGS. 2A and 2B. The shutter 120 is optionally attached to the reactor 10. In one embodiment, the shutter 120 has its own support and activation mechanism (not shown). When the shutter 120 is open, solar radiation is permitted to enter into the reactor 10, thereby producing heat. When the shutter 120 is closed, solar radiation is prevented from entering the reactor 10, and the heat inside the reactor is conserved while re-radiation is prevented. The use of the shutter 120 in open and closed modes promotes the efficiency of the thermochemical reactions carried out in the reactor 10. No external heating is used to carry out the thermochemical reactions in the reactor 10. In an embodiment, the solar radiation which the aperture 40 receives is in the form of concentrated radiation.

Referring back to FIGS. 1A and 1B, the inner member 30, outer member 20, face plate 90 and rear plate 100 are made of any material which is capable of withstanding the temperatures used to carry out thermochemical reactions in the reactor 10. Exemplary materials include refractory materials, specifically ceramics, more specifically zirconia, silicon carbide, zinc and alumina oxides or mixtures thereof. In an embodiment, the front plate 90 and rear plate 100 comprises grooved seals, specifically, metal enforced grooved seals, and more specifically graphite metal enforced seals, to fit over the ends of the inner member 30 and the outer member 20.

The dual cavity design of the reactor 10 maximizes the effective absorbance of solar radiation in the reactor 10 and minimizes re-radiation losses. The use of a vacuum reduces the temperatures used to carry out thermochemical reduction reactions in the solar thermochemical reactor 10.

In another exemplary embodiment, as depicted in a cross section of the reactor assembly shown in FIG. 2A, the outer member 20 of the reactor 10 further comprises an insulating material 130. The insulating material 130 is internal or external to the outer member 20. The outer member 20 also comprises a magnetic coil 140. In an embodiment, the magnetic coil 140 is affixed or disposed externally to or within at least part of the outer member 20 or disposed externally to the outer member 20. In another embodiment, the magnetic coil 140 is physically separate from the outer member 20 and placed in a position external and adjacent to the outer member 20. Affixing or disposing the insulation material and magnetic coil so as to form part of the outer member 20 of the reactor assembly 10 is desirable for commercial packaging and efficiency of use. The magnetic coil 140 is used to apply a magnetic field to the outer member 20 and thereby magnetically stabilizes the reactor materials 70 inside the outer cavity 60 of the reactor assembly 10.

The reactor material 70 comprises particles which are capable of becoming magnetically stabilized. Exemplary materials are described in detail in U.S. Provisional Patent Application No. 61/505,890 filed on Jul. 8, 2011, which is incorporated by reference in its entirety herein. Specifically, exemplary reactor materials 70 include metal oxides such as iron, iron oxides or mixtures thereof. More specifically, exemplary reactor materials 70 are selected from the group consisting of $Fe_2O_3$, $Fe_3O_4$, and $NiFe_2O_4$ or a combination including at least one of the foregoing. In an embodiment, the metal oxide reactor materials 70 are non-volatile. Another group of exemplary reactor materials 70 are carbonaceous materials. An example of such carbonaceous materials are activated carbon. Activated carbon is also called activated charcoal or activated coal and is a form of carbon that is riddled with small, low-volume pores that increase the surface area available for adsorption or chemical reactions. The activated carbon is mixed into ferrite powder and oxidized using either air or steam to form the reactor material 70. During the oxidation, the activated carbon is converted from a solid to a gas, i.e., from carbon to carbon dioxide. Since the activated carbon is all converted to carbon dioxide during the oxidation, the resulting reactor material contains only the oxidized porous ferrite powder. Non-volatile metal oxides, when used solar thermochemical reactions, avoid undesirable properties associated with volatile metal oxides associated with rapid quenching.

The reactor materials 70 form a bed of reactor materials within the outer cavity 60. The bed of reactor materials is then fluidized. When a magnetic field is applied to the outer member 20, and solar radiation is disposed upon the aperture 40, the temperature is elevated, and the bed of reactor materials 70 becomes magnetically stabilized. Iron powder sinters at 550° C. when oxidized. Therefore, the magnetically stabilized bed is sintered at a relatively low temperature. This results in sintering of the reactor materials 70 into a state in which the surface area is not substantially reduced. The exposure to a magnetic field has the effect of freezing the reactor materials 70 into a structure with a high surface area. The particle chains within the reactor materials 70 repel each other due to the magnetic force, creating a high surface area structure with high porosity which can withstand exposure to relatively high temperatures during the first reduction reaction of the redox cycle. In an embodiment, the magnetic field is only used during synthesis of the magnetically stabilized bed structure prior to the first reduction reaction carried out in the solar reactor using the reactor materials 70. The magnetically stabilized bed of reactor materials can overcome the sintering problems associated with other reactive materials which become sintered such that the surface area is reduced, and therefore undergo favorable chemical kinetics during reactor cycles. Accordingly, the reactor materials 70 disclosed herein avoid deactivation due to undesirable sintering and are capable of being used for many repeated reaction cycles in the reactor 10 without requiring new reactor materials to be loaded into the reactor.

The dual cavity design of the reactor 10 and magnetically stabilized reactor materials 70 used therein are used at relatively low pressures, thereby overcoming the challenges of other reactor systems which use high temperatures and high pressures. The reaction temperatures in the reduction reaction are lowered by lowering the partial pressure of the oxygen evolving as a result of the reaction. The low pressure utilized also allows for lower temperature conditions for carrying out the reduction reaction in the reactor 10. In an exemplary embodiment, the dual cavity solar thermochemical reactor 10 is operated at partial oxygen pressures of less than about $10^{-4}$ bar, specifically less than $10^{-3}$ bar, and more specifically less than $5 \times 10^{-4}$ bar to facilitate the disassociation of the metal in the reactor material 70. In another exemplary embodiment, the dual cavity solar thermochemical reactor may be operated at temperatures of less than 1500° C., specifically less than 1500° C., and more specifically less than 1450° C. In another embodiment, the dual cavity design of the reactor 10 has a low thermal mass and is equipped with a control system to control irradiation in order to cope with transient periods of availability of solar radiation. In addition, waste heat from the reactor discharge gases are recouped, and transferred to the inlet reactants, $H_2O$ and $CO_2$, to increase energy conversion efficiency.

Fracturing, caused by matrix mismatch or spallation of the metal oxide reactor material 70 is controlled by controlling the growth conditions, specifically the film thickness and/or rate of growth. In another embodiment, short duration redox cycles are used to avoid spallation and fracture. In yet another embodiment, use of a magnetically stabilized fluidized bed of reactor materials 70 avoids fracturing and spallation.

Disclosed herein too is a method of using a solar thermochemical reactor comprising disposing an inner member within an outer member, wherein the outer member surrounds the inner member, disposing a reactive material capable of being magnetically stabilized in between the outer member and the inner member, applying a vacuum to the outer member, fluidizing the reactive material, applying a magnetic field at least partially around the outer member; disposing solar radiation onto the outer member, carrying out a reduction reaction in the reactor, extracting oxygen from the outer member; disposing carbon dioxide and water onto the reactor material, carrying out an oxidation reaction in the reactor and extracting carbon monoxide gas and hydrogen gas from the outer member.

As depicted in FIGS. 2A and 2B, the reactor 10 is used to perform thermochemical redox reactions. A complete solar thermochemical reactor redox cycle comprises a reduction reaction and an oxidation reaction to produce syngas. The resulting syngas is then stored or further refined into fuels for commercial use. As depicted in FIG. 2A, in reduction mode, the reactor 10 uses concentrated solar radiation to produce heat and elevate the temperature of the reactor 10. The reactive material 70 undergoes reduction at low pressure to produce oxygen ($O_2$), which is extracted from the reactor via the material port 80. During the reduction step, the reactor material 70, or metal oxide, undergoes disassociation wherein metal is dissociated from the metal oxide. Specifically, exemplary reduction reactions are represented by the following chemical equations:

$$Fe_3O_4 + solar\ heat \rightarrow 3FeO + 0.5O_2$$

$$Fe_2O_3 + solar\ heat \rightarrow 2FeO + 0.5O_2$$

$$NiFe_2O_4 + solar\ heat \rightarrow NiFe_2O_3 + 0.5O_2$$

In an embodiment, the reduction of reactive materials 70 in the solar thermochemical reactor 10 results in reduction to iron, although this is less probable than the equations represented above, and is represented by the following exemplary chemical equation:

$$Fe_3O_4 + solar\ heat \rightarrow 3Fe + 2O_2$$

In an exemplary embodiment, as depicted in FIGS. 1A and 2A, reactive material 70 is disposed in the outer cavity 60 of the reactor 10. A vacuum is applied to the reactor assembly 10 creating a fitted seal between the outer member 20, the inner member 30, the front plate 90 and rear plate 100, aided by the grooved seals 110. The reactive material 70 is then fluidized. A magnetic field is applied to the bed of reactive material 70 via the magnetic coil 140, magnetically stabilizing the reactive material 70. The shutter 120 is opened, allowing concentrated solar radiation to be received into the reactor through the aperture 40. The magnetic field is then turned off. The concentrated radiation produces heat, elevating the temperature in the reactor 10 to sinter the reactor materials 70 and to drive the reduction reaction. The magnetically stabilized, sintered reactive material 70 undergoes reduction to produce oxygen gas, which is extracted from the reactor via the material port 80.

After the thermochemical reduction reaction is complete, the shutter 120 is closed, preventing solar radiation from entering the aperture 40 of the outer member 20. The reactor 10 is then used to carry out a thermochemical oxidation reaction in oxidation mode. The closed shutter 120 allows heat generated in the reactor to be retained and helps to minimize radiation loss.

In an exemplary embodiment, as depicted in FIG. 2B, in oxidation mode, water ($H_2O$) and carbon dioxide ($CO_2$) are introduced into the reactor 10 via the material port 80 to oxidize the magnetically stabilized bed of reactive material 70. The reactive material 70 undergoes oxidation at atmospheric pressure to produce carbon monoxide and hydrogen gases, or syngas, which is extracted from the reactor via the material port 80. The heat produced from the exothermic oxidation reaction is sufficient to maintain the temperature. Specifically, exemplary oxidation reactions are represented by the following chemical equations:

$$3FeO + H_2O + CO_2 \rightarrow Fe_3O_4 + H_2 + CO$$

$$2FeO + H_2O + CO_2 \rightarrow Fe_2O_3 + H_2 + CO$$

$$3Fe + 4H_2O + CO_2 \rightarrow Fe_3O_4 + 4H_2 + CO$$

$$2NiFe_2O_3 + H_2O + CO_2 \rightarrow 2NiFe_2O_4 + H_2 + CO$$

The thermochemical reduction reaction and oxidation reaction together constitute a single redox cycle. The resulting syngas is refined into fuel for commercial use or stored for later refinement. In an embodiment, the magnetically stabilized bed material is used for many cycles, specifically many hundred cycles, and more specifically thousands of cycles, before being replaced. In another embodiment, the redox reactions are carried out in short duration cycles. For example, a complete redox cycle is carried out in about one hour, more specifically in about 15 minutes.

Figure 3:
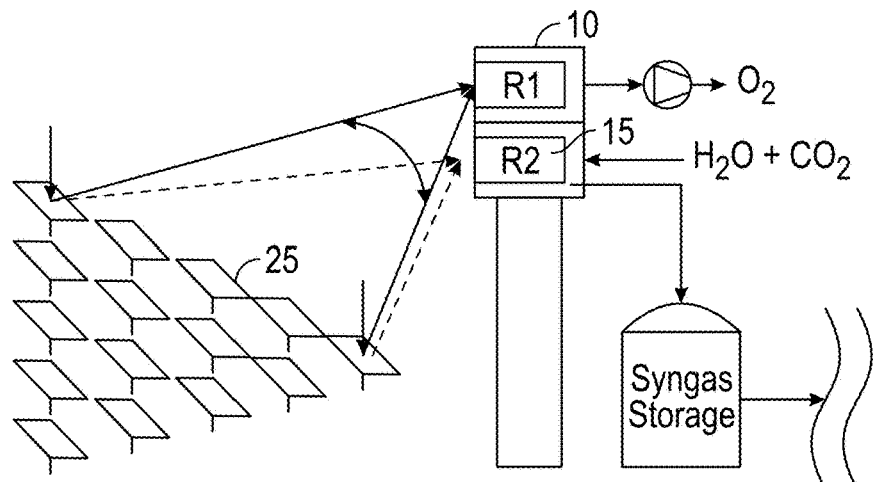
FIG. 3 is a depiction of an exemplary cyclic looping process using two solar thermochemical reactors in close proximity to one another.

In yet another exemplary embodiment, a looping process is provided as depicted in FIG. 3. As shown in FIG. 3, a first solar thermochemical reactor 10 is disposed in close proximity to a second solar thermochemical reactor 15. Concentrated radiation, such as that from an adjustable heliostat field 25, is focused onto the first reactor 10 wherein the shutter is open. A reduction reaction as described above is carried out and once completed, the shutter is closed, allowing the oxidation reaction to produce syngas to proceed. Once the reduction reaction in the first reactor 10 is completed, and while the oxidation reaction is being carried out in the first reactor 10, the concentrated solar radiation is refocused onto the second reactor 15, which similarly undergoes a reduction reaction. Once the reduction reaction in the second reactor 15 is completed, the concentrated solar radiation is again refocused from the heliostat 25 onto the first reactor 10, and the looping process begins again. The looping process maximizes efficiency by increasing the use of available solar radiation during the redox cycle. This looping process uses two or more reactors located in close proximity to each other. The looping process is repeated over and over, thus minimizing downtime during periods when solar radiation is available between redox cycles. The looping process and reactor system have a solar-to-chemical fuel conversion efficiency of about 10%, specifically about 25% or greater based on a 1 MW scale reactor design. The looping process overcomes the challenges associated with the cyclical and transient nature of solar thermochemical reactor operation.

Two or more reactors in close proximity to one another are used in the looping process. In one embodiment, at least two reactors are disposed side-by-side. In another embodiment, at least one reactor is disposed on top of at least one other reactor. In another embodiment, the shifting of the solar radiation onto to reactor is accomplished by shifting a heliostat to move the concentrated solar radiation from one reactor to another. In another embodiment, two or more reactors are disposed upon a rotating reactor assembly which refocuses concentrated solar radiation from one reactor to another. In yet another embodiment, a beam-redirected mirror is used to refocus concentrated solar radiation from one reactor to another.

In an exemplary embodiment, a solar reactor having a dual cavity design as described above has an aperture 40 that does not include an optically transparent material, operates at a relatively a low pressure and temperature to carry out the metal dissociation reduction step, and magnetically stabilized reactor materials are sintered in a controlled manner to avoid undesirable sintering and deactivation of the metal reactor materials.

Figure 4:
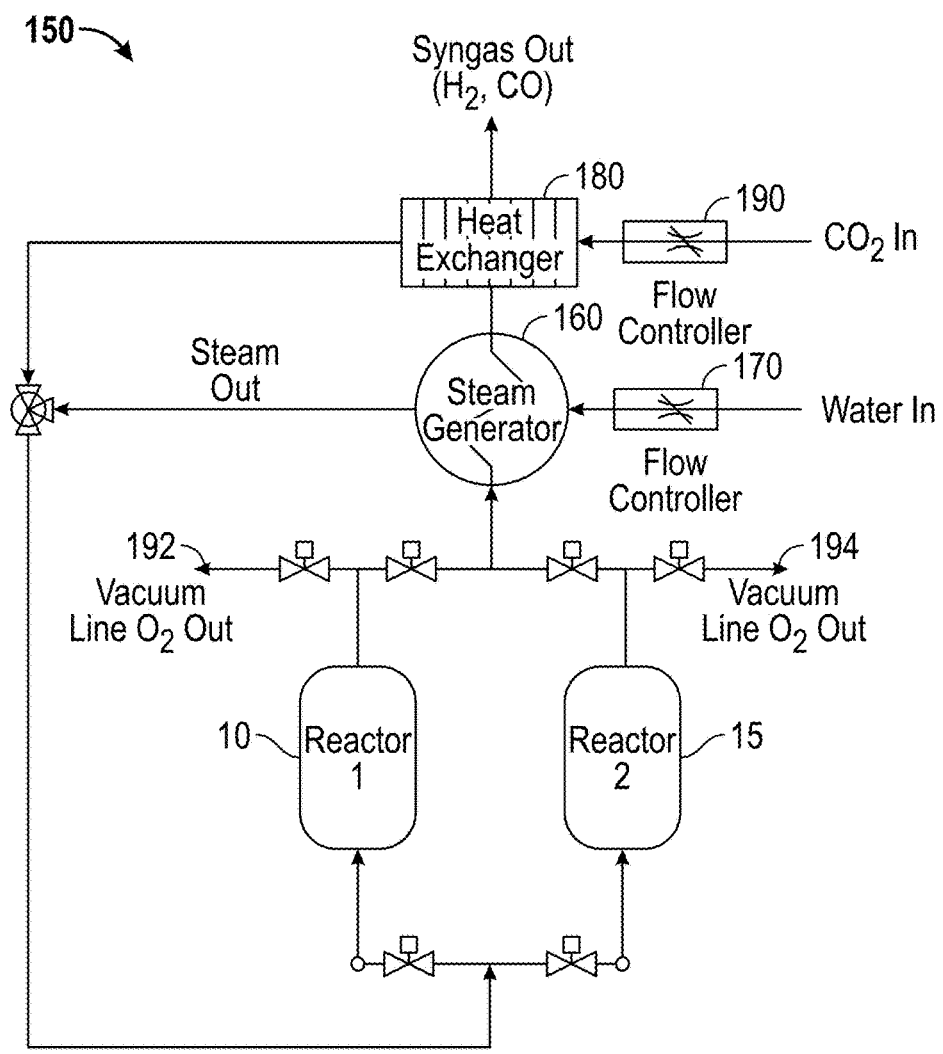
FIG. 4 is a depiction of an exemplary reactor setup.

In another embodiment, as depicted in FIG. 4, a reactor system 150 is equipped with means to automatically carry out the redox cycles. The reactor system 150 comprises a first solar thermochemical reactor 10 disposed in close proximity and in fluid communication with a second solar thermochemical reactor 15. A steam generator 160 is disposed upstream from and in fluid communication with the first solar thermochemical reactor 10 and the second solar thermochemical reactor 15. A first controller 170 is disposed upstream of the steam generator 160 from which water is supplied. The first controller 170 controls the flow rate of water supplied to the steam generator 160. In an embodiment, the flow rate of the water entering the steam generator 160 is from about 0.1 g-$cm^2$ to about 1.0 g-$cm^2$. The steam generator 160 elevates the temperature of the water supplied by the first controller 170 to generate steam. The temperature in the steam generator 160 which is used to convert water to steam is from about 200° C. to about 500° C. The steam is then supplied from the steam generator 160 to the first solar thermochemical reactor 10 and the second solar thermochemical reactor 15 for use in the redox cycle reactions carried out therein.

The reactor system 150 further comprises a heat exchanger 180 disposed upstream from and in fluid communication with the first solar thermochemical reactor 10 and the second solar thermochemical reactor 15. A second controller 190 is disposed upstream of the heat exchanger 180 from which carbon dioxide is supplied. The second controller 190 controls the flow rate of carbon dioxide supplied to the heat exchanger 180. In an embodiment, the flow rate of the carbon dioxide entering the heat exchanger 180 is from about 0.1 g-cm² to about 1.0 g-cm². The heat exchanger 180 elevates the temperature of the carbon dioxide supplied from second controller 190. The temperature in the heat exchanger 180 which is used to elevate the temperature of the carbon dioxide is from about 25° C. to about 400° C. The carbon dioxide is then supplied from the heat exchanger 180 to the first solar thermochemical reactor 10 and the second solar thermochemical reactor 15 for use in the redox cycle reactions carried out therein.

The reactor system 150 further comprises means for heat recuperation. A first vacuum pump 192 and a second vacuum pump 194 are disposed downstream of and in fluid communication with the first solar thermochemical reactor 10 and the second solar thermochemical reactor 15. The first vacuum pump 192 and second vacuum pump 194 remove oxygen produced from the redox cycle reactions which occur in the reactors. Heat generated from the redox cycle reactions carried out in the first solar thermochemical reactor 10 and the second solar thermochemical reactor 15, and the hydrogen and carbon monoxide reaction products, are supplied to the steam generator 160 where the heat is used to generate steam from water. The heat is supplied from the steam generator 160 to the heat exchanger 180 where the heat is used to elevate the temperature of the carbon dioxide reaction product and the reaction products are collected. In another embodiment, the reactor system 150 also includes other heat recuperation technology.

Disclosed herein too is a solar thermogravimeter for modeling the kinetics of thermochemical reactions in a solar thermochemical reactor. The thermogravimeter facilitates modeling of thermochemical reactions to optimize reaction conditions and increase efficiency of operations in a solar reactor.

Figure 5B:
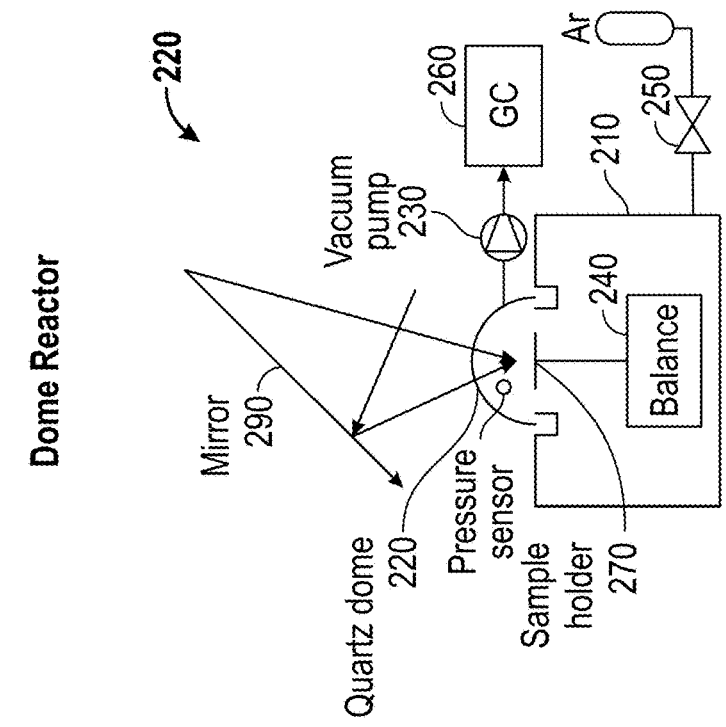
FIG. 5B is a depiction of an exemplary thermogravimeter using a dome-shaped reactor.
Figure 5A:
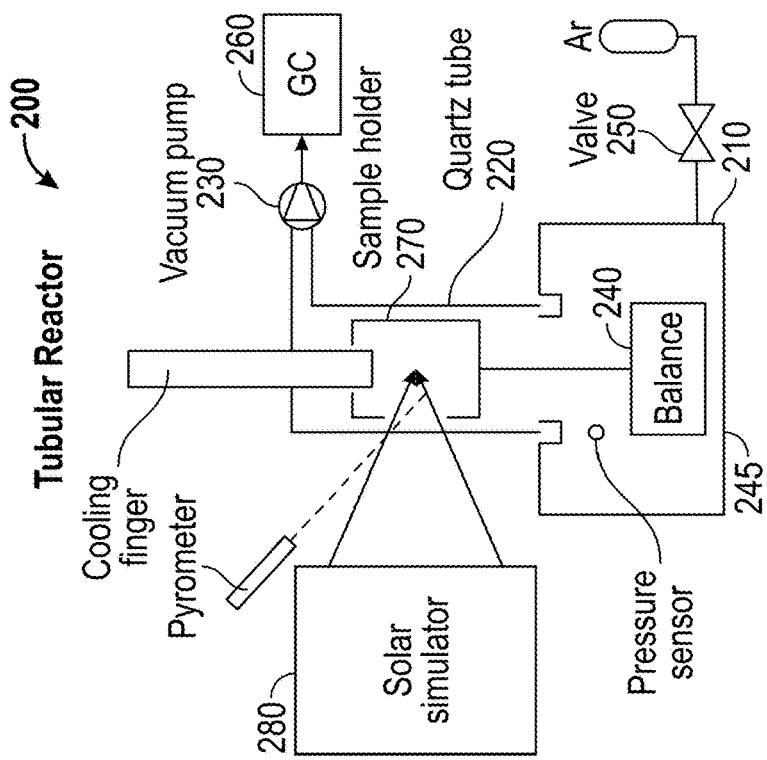
FIG. 5A is a depiction of an exemplary thermogravimeter using a tubular-shaped reactor.

In an exemplary embodiment, a thermogravimeter is assembled as shown in FIGS. 5A and 5B. The solar thermogravimeter 200 comprises a metal pressure vessel 210, a tubular or dome shaped quartz vessel 220 for optical access, a low vibration vacuum pump 230, an analytical balance 240 disposed within the low pressure vessel, a temperature sensor (not shown), a thermocouple (not shown), a flow meter 250 and a gas phase chromatograph or a mass spectrometer 260. An analytical balance 240 is placed inside a vacuum chamber 245. A sample placed in a sample holder 270 is directly irradiated by intense thermal radiation from a high flux solar simulator 280. In another embodiment, instead of a solar simulator, a mirror which reflects solar radiation is used. The temperature and pressure conditions closely approach those inside a solar reactor. In an embodiment, the thermogravimeter 200 is a tubular, horizontally illuminated reactor or a dome-shaped, vertically illuminated reactor. The temperature sensor is a remote temperature sensor, specifically an IR pyrometer. The IR pyrometer is equipped with a fast shutter that blocks radiation from the solar simulator or mirror for short times to minimize IR pyrometer miss-readings due to spill radiation.

The invention is exemplified by the following non-limiting examples.

EXAMPLES

Example 1

Figure 6:
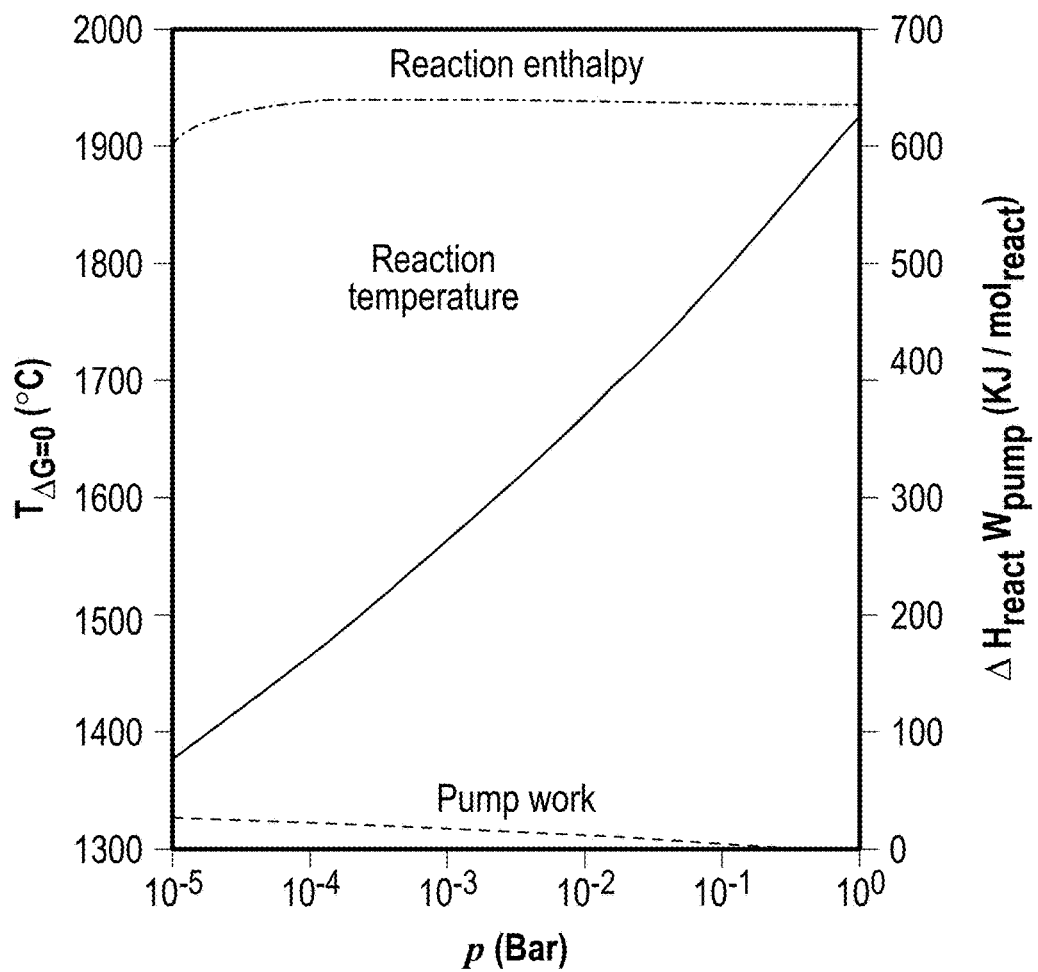
FIG. 6 is a graph showing the disassociation temperature, reaction enthalpy, and losses due to pump work as a function of absolute pressure for the iron oxide reactor material matrix, specifically, the disassociation temperature as a function of pressure for the purely thermal reduction reaction temperature for which the Gibbs free energy change of reaction equals zero.

As shown in FIG. 6, the theoretical data in the graph shows the disassociation temperature, reaction enthalpy, and losses due to pump work as a function of absolute pressure for the iron oxide reactor material matrix, specifically, the disassociation temperature as a function of pressure for the purely thermal reduction reaction temperature for which the Gibbs free energy change of reaction equals zero. The graph also shows the reaction enthalpy per mole of the reaction and the required pump work for isothermal compression after cooling to about 300° K per mole of the reaction. In addition, the graph shows that the pump work is one to two orders of magnitude smaller than the reaction enthalpy, allowing for low pressure solar reduction.

Figure 7:
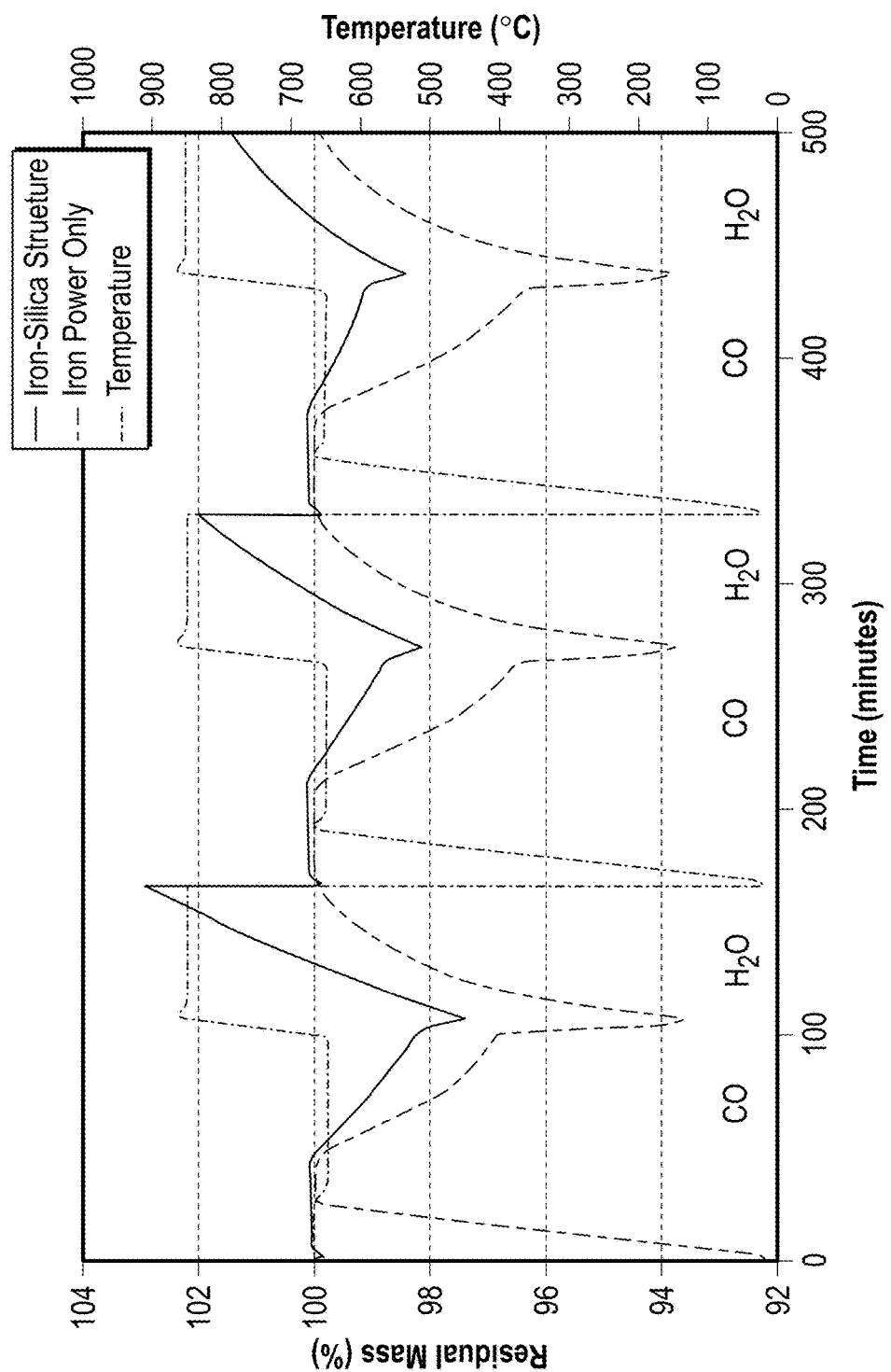
FIG. 7 show the output from a thermogravimetric analysis (TGA) demonstrating the cyclic reactivity for three redox cycles.

The output from a thermogravimeter demonstrating the cyclic reactivity for three redox cycles is shown in FIG. 7. The thermogravimeter measures the reaction kinetics for different test materials. The balance measures the mass of the reactive material. When the reactive material is reduced, the mass of the sample decreases due to the release of oxygen. When the sample is oxidized, the mass of the sample is increased due to the addition of oxygen.

Example 2

This example was conducted to demonstrate the manufacturing of the monolithic solid (reactor bed materials 70—referring to the FIGS. 2A and 2B) using activated carbon instead of silica. The activated carbon is mixed into ferrite powder and oxidized using either air or steam. In this manner, the activated carbon is converted from a solid to a gas, i.e., from carbon to carbon dioxide. Since the activated carbon is all converted to carbon dioxide during the oxidation, the oxidation of the activated carbon results in the formation of voids and pores in the ferrite material. The resulting porous solid thus contains only the oxidized ferrite powder.

To test this approach, a 0.1 g sample of the activated carbon was tested in a thermogravimeter and oxidized using a flow of 100 cubic centimeters of air during a temperature ramp to 1000° C. at 5° C./min. The results of this test are seen in the FIG. 6.

Figure 8:
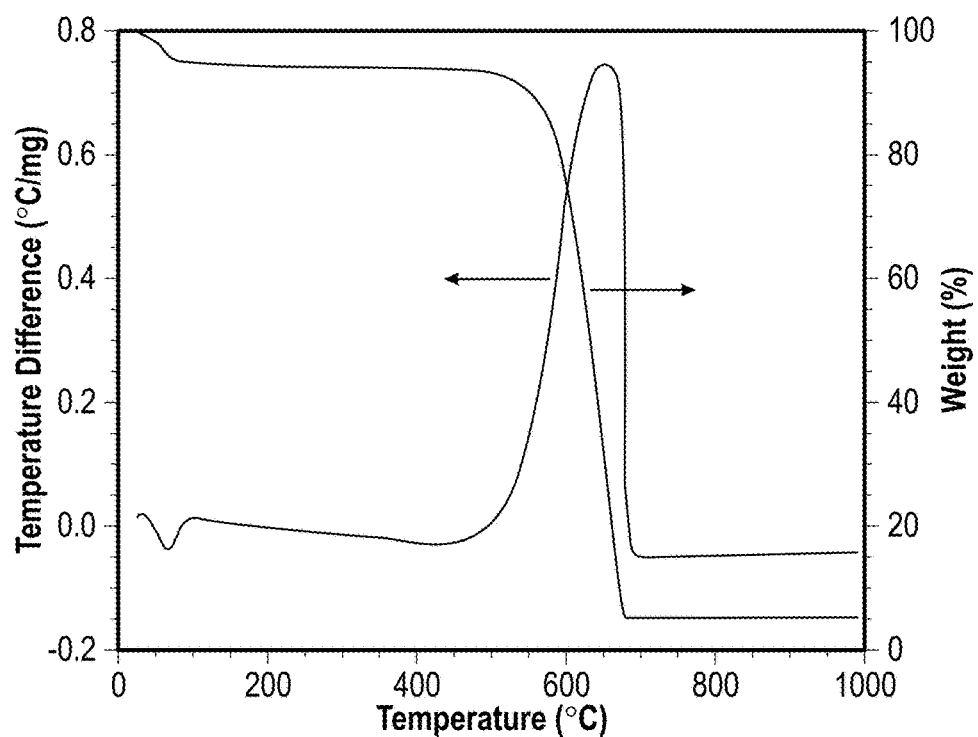
FIG. 8 is a graph showing thermogravimetric analysis (TGA) results for the oxidation of activated carbon during a temperature ramp to 1000° C. at 5° C./min.

It can be seen above that the onset of oxidation occurs at approximately 500° C. and rapid mass loss proceeds. While the FIG. 8 shows that 5% mass remains at the end of the cycle, this is in error due to instabilities occurring at the beginning of the cycle. This is why there is also a 5% decrease in weight at the beginning of the test. This is validated by the fact that at the end of the test, there was no material left in the crucible.

Figure 9:
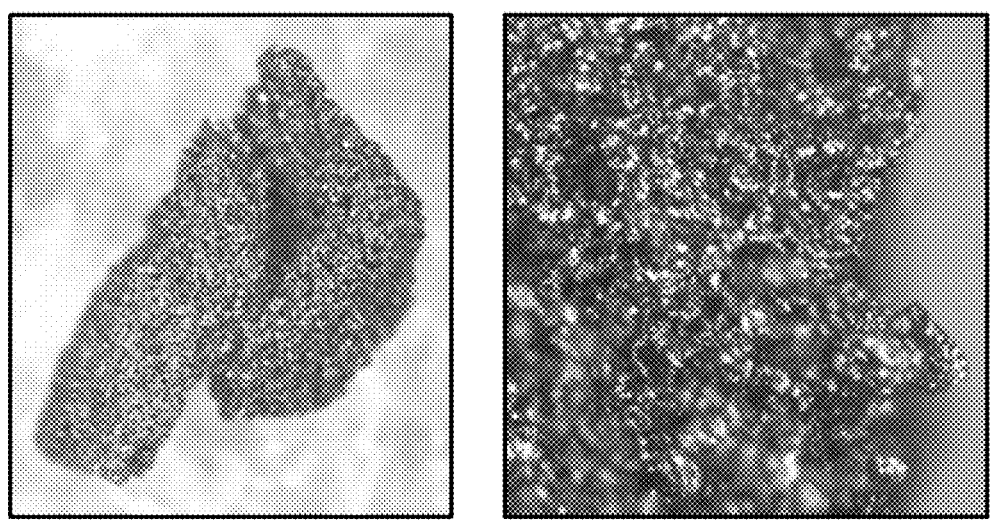
FIG. 9 shows photomicrograph (at two different magnifications) of the monolithic solid after the activation of carbon is completed.

The procedure for making a porous structure (i.e., the monolithic solid) is as follows. Ferrite powder (crushed and sieved to 75 to 125 micrometer size) and activated carbon (as received, Fisher Chemical, catalog number C272500) are mixed thoroughly together and placed into a quartz tube reactor. The mixture is then slowly heated (10° C./min) using an inert gas (Nitrogen/Argon) to 1000° C. The mixture is then reduced using a reducing gas (5% $H_2$ in Ar) to bring the ferrite powder to its lowest oxidation state. This procedure has no effect on the activated carbon (already fully reduced). Following this, the powders are then oxidized using steam at low flow rates at the same temperature as reduction (1000-1200° C.). This allows for the oxidation of both the ferrite powder (Fe to $Fe_3O_4$, Co to $Co_3O_4$) and the activated carbon (C to $CO_2$). However, since the activated carbon becomes a gas and the ferrite powder sinters, the resulting structure after oxidation is a porous monolithic solid in a ferrite matrix. The voids exist where the activated carbon once had been. Images of a resulting ACOS structure are shown below in FIG. 9. The resulting porous sintered structure remains stable after repeated oxidation and reduction cycles at temperatures up to 1500° C. Thus, this structure is very useful for a cyclical looping process that requires thermal reduction at temperatures up to 1400° C. Such a looping process can be used to produce syngas by splitting water and carbon dioxide using concentrated solar radiation in conjunction with the porous metal ferrite structure.

From this example, it may be seen that the activated carbon may be consumed or converted during the formation of the monolithic solid. Thus the monolithic solid may comprise a plurality of porous ferrite particles that are bonded together. In one embodiment, the activated particles can be consumed after the formation of the monolithic solid, leaving behind a porous monolithic solid that comprises only a plurality of ferrite particles that are lightly bonded together.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the invention not be limited to the particular embodiment disclosed as the best mode contemplated for carrying out this disclosure.

What is claimed is:

1. A method of using a solar thermochemical reactor comprising:
    providing a solar thermochemical reactor including an outer member;
    disposing an inner member within the outer member, wherein the outer member surrounds the inner member;
    disposing a reactive material capable of being magnetically stabilized in between the outer member and the inner member;
    applying a vacuum to the outer member after disposing the reactive material;
    fluidizing the reactive material after applying the vacuum;
    applying a magnetic field around the outer member after fluidizing the reactive material;
    causing solar radiation to be received by the outer member while the magnetic field is applied;
    carrying out a reduction reaction in the reactor to produce oxygen, the reduction reaction being carried out after causing the solar radiation to be received;
    extracting the oxygen from the outer member;
    disposing carbon dioxide and water onto the reactor material after extracting the oxygen;
    carrying out an oxidation reaction in the reactor to produce carbon monoxide gas and hydrogen gas; and
    extracting carbon monoxide gas and hydrogen gas from the outer member.

2. The method of claim 1, wherein the reduction reaction is carried out at a temperature of less than or equal to 1500° C.

3. The method of claim 1, wherein the oxidation reaction is carried out at an autothermal temperature.

4. The method of claim 1, wherein the reduction reaction is carried out at a pressure of less than or equal to $10^{-4}$ bar.

5. The method of claim 1, wherein the oxidation reaction is carried out at atmospheric pressure.

* * * * *